United States Patent [19]
Palli et al.

[11] Patent Number: 5,891,431
[45] Date of Patent: Apr. 6, 1999

[54] TRANSGENIC VIRUS

[75] Inventors: Subba Reddy Palli; Basil M. Arif; Sardar S. Sohi; Arthur Retnakaran, all of Marie, Canada

[73] Assignee: Her Majesty the Queen in right of Canada, as represented by the Minister of Natural Resources, Ottawa, Canada

[21] Appl. No.: 787,398

[22] Filed: Jan. 22, 1997

[51] Int. Cl.$^6$ .............................. A01N 63/00; C12N 7/01; C12N 15/86

[52] U.S. Cl. .................. 424/93.2; 435/235.1; 435/320.1; 47/58.1

[58] Field of Search .............................. 435/320.1, 235.1; 424/93.2; 47/58.1

[56] References Cited

PUBLICATIONS

Winter, J. et al. Virology 211: 462–473, 1995.
Insecticidal Effects of an Insect–Specific Neurotoxin Expressed by a Recombinant Baculovirus, Maeda et al, Department of Entomology, University of California, Apr. 26, 1991, pp. 777–780.
Insecticidal Activity of a Bacterial Crystal Protein Expressed by a Recombinant Baculovirus in Insect Cells; Martens et al, Department of Virology, Agricultural University Wageningen, Apr. 26, 1990, pp. 2764–2770.
Expression and Effects of the juvenile hormone esterase in a baculoviruc vector; Hammock et al, NERC Institute of Virology, Nature vol. 344, Mar. 29, 1990, pp. 458–461.
Increased Insectional Effect by a Recombinant Baculovirus Carrying a Synthetic Diuretic Hormone Gene, Susumu Maeda, Zoecon Research Institute, Biochemical and Biophysical Research Communications, vol. 165, No. 3, Dec. 29, 1989, pp. 1177–1183.
Cummingham and House, 1984, *Choristoneura fumiferana* (clemens), Spruce budworm (Lepidoptera: Torticidae); B. Viruses: Application and Assessment. In Biological Control Programmes against Insect and Weeds in Canada 1969–1980, Kelleher, J.S. and Hulme, M.A., eds., Commonwealth Agricultural Bureau, Slough, England).
Bonning et al, Annu. Rev. Entomol. 85:437–446.
Coordination of larval and prepupal gene expression by the DHR3 orphan receptor during Drosophila metamorphosis, Lam et al., Development, 1997, 124: 1757–1769.
Genetic modification of an entomopoxvirus: deletion of the spheroidin gene does not affect virus replication in vitro, Palmer et al., J. Gen. Virol., 1995, 76:15–23.
Insecticidal activity of a recombinant baculovirus containing an antisensee c–myc fragment, Lee et al., J. Gen. Virol., 1997, 78:273–281.
Transient, nonlethal expression of genes in vertebrate cells by recombinant entomopoxviruses, Li et al., J. Virol, 1997, 71:9557–9562.

*Primary Examiner*—Mary E. Mosher

[57] ABSTRACT

The present invention describes a new kind of transgenic virus which comprise insect transcription factors. Specifically, the transgenic insect virus comprises insect transcription factors that are involved in molting and metamorphosis. Such transgenic insect viruses are useful as biopesticides.

14 Claims, 4 Drawing Sheets

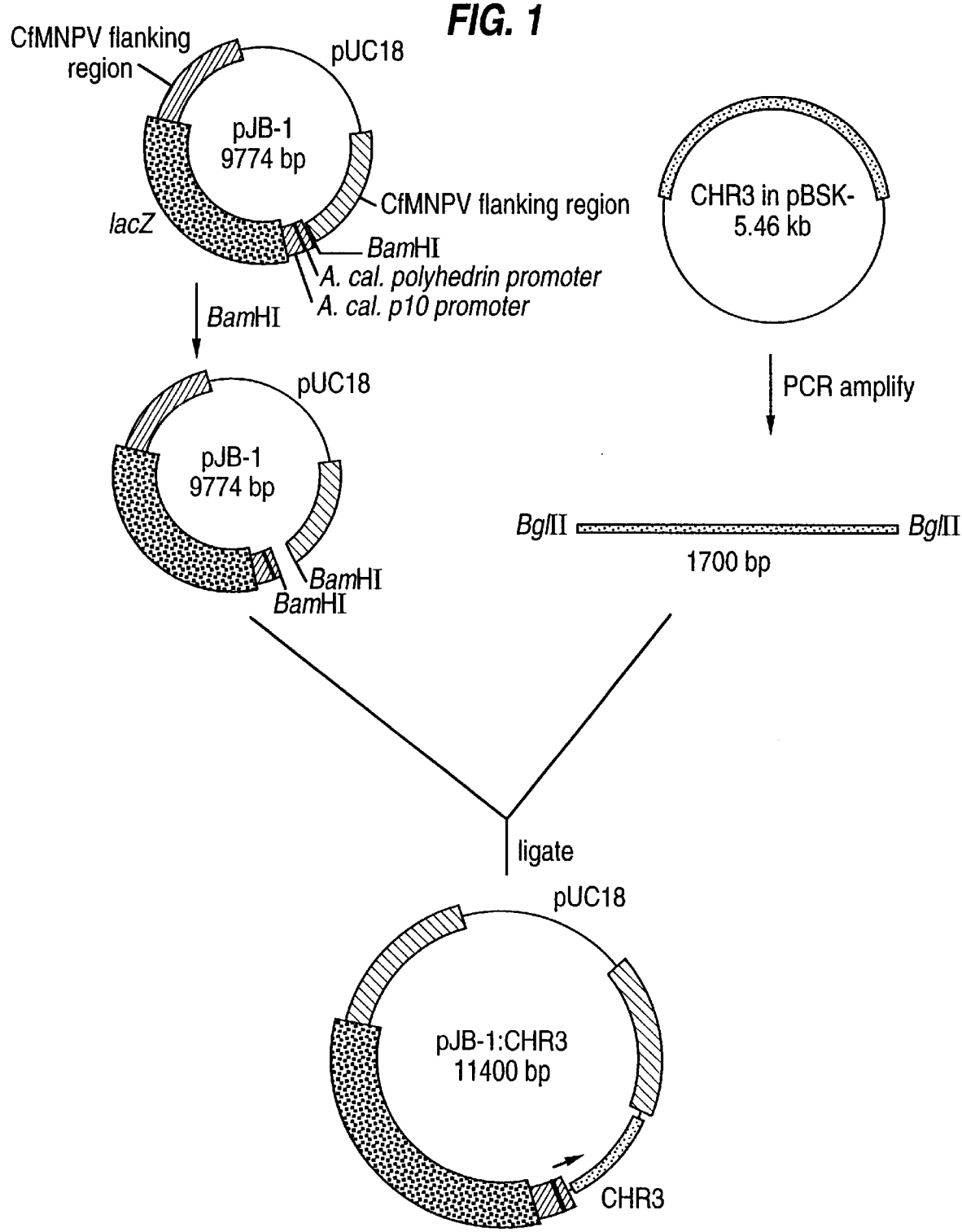

TRANSGENIC VIRUS

TECHNICAL FIELD OF THE INVENTION

The present invention is directed to transgenic insect viruses comprising insect transcription factors. In particular, the invention is related to transgenic insect viruses comprising insect transcription factors involved in molting and metamorphosis. Such transgenic insect viruses are useful as biopesticides.

BACKGROUND OF THE INVENTION

Traditionally pest control has been dominated by the use of chemical insecticides. Although they are fast acting, these chemicals are sometimes environmentally unattractive. In addition, many chemicals used in insect pest control are not species-specific and may affect non-target vertebrates and invertebrates as well as the target pest. These chemicals or their by-products can sometimes persist in the environment for long periods of time.

The development and use of pest biology, population dynamics, silvicultural practice, natural control agents (i.e., parasitoids, pathogens), and improved operational forest pest management practices are new tools for forest management. Biological control, the use of living organisms to control insect pests, has become increasingly more acceptable as a means of successfully controlling pests. For example, the bio-insecticide *Bacillus thuringiensis* (Bt), is used for control of spruce budworm and gypsy moth larvae. However, some recent concerns over the specificity of Bt have resulted in the recommendation that it not be used in areas where there are endangered Lepidoptera. Ecological interests have resulted in a shift in emphasis to examine and develop other microbial products, including the insect viruses.

Insect viruses are naturally occurring insect pathogens that are considered to be host specific and environmentally safe. They can persist from year to year to impact on several generations of insects. There are over 1200 insect viruses (nucleopolyhedroviruses, granulovirus, entomopoxviruses, cypovirus and others) that have potential for insect control.

One problem associated with several natural insect viruses is that there is a time delay between the viral entry into the insect body and the lethal infection. Insect viruses must be ingested by larvae to allow infection. Occlusion bodies containing virus particles contaminating the foliage are eaten and dissolved by the insect's midgut juices, releasing virus particles. These particles pass through the gut cells and infect tracheal and other body tissues of the host larva. Over a typical period of 15 days, the virus replicates in susceptible tissues eventually causing death. Infected larvae still feed, during this time; however, and hence significant defoliation of plants still can occur in the time interval between ingestion of virus and insect death. This feeding damage is an inherent problem with using natural insect viruses.

Another problem associated with natural insect viruses is lack of virulence. For example, extensive field trials have shown that the spruce budworm nucleopolyhedrovirus (CfMNPV) will infect populations of spruce budworm, but has not caused epizootics that result in large scale mortality and population reduction (Cunningham and House, 1984, *Choristoneura fumiferana* (clemens), Spruce budworm (Lepidoptera: Tortricidae); B. Viruses: Application and Assessment. In Biological Control Programmes against Insect and Weeds in Canada 1969–1980, Kelleher, J. S. and Hulme, M. A., eds., Commonwealth Agricultural Bureau, Slough, England).

Many strategies have been adopted to decrease the feeding damage caused by infected insects. One strategy is the application of virus formulations containing "virus enhancers" to early instar larvae so that infection occurs faster, preventing serious defoliation. Unfortunately, this strategy cannot be used if the insect is evasive or if large amounts of the insect virus are unavailable. Such is the case for the control of the spruce budworm, *Choristoneura fumiferana* (Clem), with nucleopolyhedrovirus.

The development of biotechnology provides tools to genetically modify insect viruses to enhance their effectiveness. Genes encoding toxins (scorpion/mite toxin), enzymes (juvenile hormone (JH) esterase), neuropeptides (prothoracicotropic hormone), and eclosion hormone have been introduced into the viral genome by various research groups (Bonning et al., Annu. Rev. Entomol. 85: 437–446). These genes encode secretory proteins or peptides which assert their functions outside of virus infected cells. Inserting the JH esterase gene into the alfalfa looper nucleopolyhedrovirus (AcMNPV) results in the secretion of the enzyme JH esterase into the hemolymph and improves the virus as a control agent. Scorpion toxin and mite toxin have also been inserted into AcMNPV. These proteins are neurotoxins that are secreted into the hemolymph and act on the nervous system. A major drawback of these transgenic viruses is that the foreign genes encode secretory products which have to act outside of infected cells, e.g., in the hemolymph. These gene products run the risk of being degraded or eliminated by the insect's detoxifying system.

There is still a need to develop new transgenic viruses as biopesticides. Especially there is a need to construct transgenic viruses by introducing new types of foreign genes into the viral genome.

SUMMARY OF THE INVENTION

This invention provides a transgenic insect virus useful as a biopesticide.

The invention also provides a transgenic insect virus that is fast acting and has an enhanced virulence as compared to an unmodified virus.

The invention produces a transgenic virus which encodes a protein factor functioning inside instead of outside the infected cells.

Finally, the invention provides an insecticide composition containing the transgenic insect virus of the invention, which can be used to control insect populations.

These and other objects of the invention are provided by one or more of the embodiments described below.

In one embodiment of the invention a transgenic insect virus is provided which contains foreign DNA encoding a developmentally regulated insect transcription factor which is operably linked to a transcription regulatory region. In a preferred embodiment, the developmentally regulated insect transcription factor is associated with insect molting and metamorphosis. Still other embodiments of the invention contemplate insecticides containing such transgenic insect viruses and their use to control insect populations.

These and other embodiments of the invention provide new types of transgenic viruses. The transgenic viruses provided by the present invention are able to make protein products functioning inside the virus infected cells and thereby bypass the problems associated with the secretory proteins of other transgenic viruses. This characteristic also enables the transgenic viruses to work quickly and efficiently as biopesticides.

BRIEF DESCRIPTION OF THE DRAWINGS

FIG. 1 shows the construction of CfMNPV transfer vector.

DETAILED DESCRIPTION OF THE INVENTION

Figure 2A:
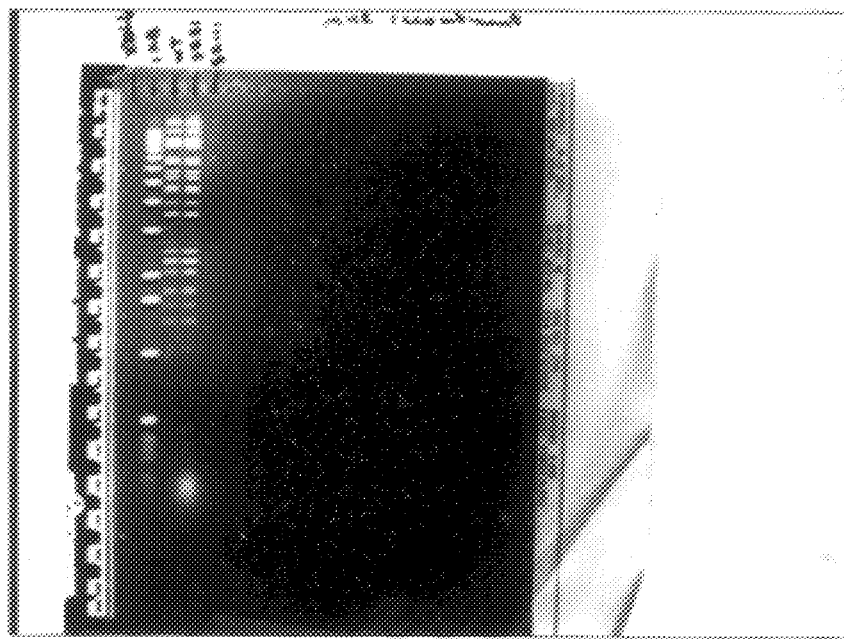
FIG. 2 demonstrates that the CHR3 DNA is inserted at the expected region of CfMNPV.

The present invention is directed to insect viruses containing developmentally regulated insect transcription factors and the control of insects therewith. In one preferred embodiment, the present invention relates to insect viruses containing foreign DNA encoding insect transcription factors involved in insect molting and metamorphosis.

A broad range of lepidopteran insects can be controlled according to this invention. Specific examples include the following:

| Virus type | Name | Target insect | Common name |
|---|---|---|---|
| Nucleopolyhedrosis virus | Anticarsia gemmatalis MNPV | Anticarsia gemmatalis | velvetbean caterpillar |
| Nucleopolyhedrosis virus | Autographa californica MNPV | Autographa californica | alfalfa looper |
| Nucleopolyhedrosis virus | Choristoneura fumiferana MNPV | Choristoneura fumiferana | spruce budworm |
| Nucleopolyhedrosis virus | Helicoverpa armigera NPV | Helicoverpa armigera | american bollworm |
| Nucleopolyhedrosis virus | Helicoverpa zea SNPV | Helicoverpa zea | corn earworm |
| Nucleopolyhedrosis virus | Lymantria dispar MNPV | Lymantria dispar | gypsy moth |
| Nucleopolyhedrosis virus | Mamestra brassiccae MNPV | Mamestra brassicae | cabbage moth |
| Nucleopolyhedrosis virus | Orgyia pseudotsugata SNPV | Orygia pseudotsugata | tussock moth |
| Nucleopolyhedrosis virus | Spodoptera exigua MNPV | Spodoptera exigua | beet armyworm |
| Nucleopolyhedrosis virus | Spodoptera frugiperda MNPV | Spodoptera frugiperda | fall armyworm |
| Nucleopolyhedrosis virus | Trichoplusia ni MNPV | Trichoplusia ni | cabbage looper |
| Granulovirus | Artogeia rapae GV | Artogeia rapae | imported cabbageworm |
| Granulovirus | Cydia pomonella GV | Cydia pomonella | codling moth |
| Granulovirus | Homona magnanima GV | Homona magnanima | tea tortrix |
| Granulovirus | Pieris brassicae GV | Pieris brassicae | european cabbageworm |
| Granulovirus | Plodia interpunctella GV | Plodia interpunctella | indian mealmoth |
| Granulovirus | Trichoplusia ni GV | Trichopiusia ni | cabbage looper |
| Entomopoxvirus A | Anomala cuprea EV | Anomala cuprea | no common name |
| Entomopoxvirus A | Aphodius tasmaniae EV | Aphodius tasmaniae | no common name |
| Entomopoxvirus B | Amsacta moorei EV | Amsacta moorei | red hairy catupillar |
| | Operophtera brumata EV | Operophtera brumata | winter moth |
| | Choristoneura fumiferana EV | Choristoneura fumiferana | spruce budworm |
| | Choristoneura biennis EV | Choristoneura biennis | spruce budworm |
| Cypovirus | Helicoverpa armigera CPV5 | Helicoverpa armigera | american bollworm |
| Cypovirus | Lymantria dispar CPV 1 | Lymantria dispar | gypsy moth |
| Cypovirus | Mamestra brassicae CPV7 | Mamestra brassicae | cabbage moth |
| Cypovirus | Pectinophora gossypiella CPV11 | Pectinophora gossypiella | pink bollworm |
| Cypovirus | Pieris rapae CPV2 | Pieris rapae | imported cabbageworm |
| Cypovirus | Spodoptera exempta CPV5 | Spodoptera exempta | african armyworm |

Any insect which is susceptible to viral infection can be a target for the practice of the present invention.

Insect viruses are naturally occurring insect pathogens. They may be DNA viruses or RNA viruses. Many insect viruses and their host range are known in the art. Any insect virus known in the art can be employed for the purpose of this invention. Preferably the insect virus used is host specific and environmentally safe. More preferably the insect virus is a DNA virus which has been traditionally used as a biological control agent on insect pests, e.g., baculovirus (nucleopolyhedrovirus and granulovirus) and entomopoxvirus. RNA viruses suitable for use in the invention include, but are not limited to cypovirus.

Any of the developmentally regulated insect transcription factors are suitable for use in the present invention. Developmentally regulated insect transcription factors are a subset of insect transcription factors. Such insect transcription factors are regulatory proteins. They often have a built-in nuclear localization signal that directs them to move into the nucleus, where they interact with DNA and exert their effects. They also have a specific DNA binding domain which binds to specific sequences in the regulatory regions of genes. Developmentally regulated transcription factors usually are produced in small amounts and are temporally and spatially regulated within an insect. Transcription factor production is generally dependent upon various hormones, e.g., they are expressed, activated, and/or inactivated by the action of insect hormones, e.g., ecdysone, juvenile hormone, and others. They are also likely to have a structure that is similar to a hormone receptor or belong to a receptor superfamily. Developmentally regulated insect transcription factors are known in the art. They include, but are not limited to Drosophila BR-C, E74, E75, Ultraspiracle, E78, Sevenup, Kni/Knrl/egon, FTZ-F1, DHR38, E93, Relish-antibacterial transcription factor, Col-head patterning transcription factor, Escargot and snail transcription factors, e.g., embryonic wing disc, Dorsal transcription factors, e.g., retrotransposon response to UV, DSX-M and DSX-F transcription factors, e.g., repression and activation of yolk protein respectively, Dif transactivating cecropin gene, Eyeless transcription factors, Gap gene kni transcription factors, Kappa B like immune genes activating transcription factor, transcription factors encoded by Zygotic genes that regulate embryonic development of the anterior and posterior termini, and DHR78, DHR96, Manduca MHR3-ecdysone inducible transcription factor, Choristoneura hormone receptor 2 (CHR2), Choristoneura hormone receptor 3 (CHR3), *Choristoneura fumiferana* ecdysone receptor (CfEcR), *Choristoneura fumiferana* ultraspiracle protein (CfUSP), Spodoptera Viral gp64 activating transcription factor, and Egr-1 master switch gene, and *Bombyx Mori* Silk protein transcription factor.

The most preferred developmentally regulated insect transcription factors are those associated with regulation of molting, reproduction, metamorphosis, and development in insects. Developmentally regulated transcription factors may trigger the expression of a specific set of genes which in turn switch on and off the genes involved in the physiological events of molting and metamorphosis. Many such transcription factors regulating molting and metamorphosis are known in the art, e.g., Choristoneura hormone receptor 2 (CHR2), Choristoneura hormone receptor 3 (CHR3), *Choristoneura fumiferana* ecdysone receptor (CfEcR), *Choristoneura fumiferana* ultraspiracle protein (CfUSP), Manduca hormone receptor 3 (MHR3), and Drosophila hormone receptor 38 (DHR38).

A transgenic or recombinant insect virus can be constructed by integrating a fragment or a contiguous foreign DNA encoding a developmentally regulated insect transcription factor into the virus genome. As known in the art, the foreign DNA may be operably or covalently linked in a cis configuration to a transcription regulatory region so that gene expression of the insect transcription factor is driven by the regulatory region usually residing 5' upstream of a gene. Alternatively, the DNA fragment may encode a fusion protein comprising a developmentally regulated insect transcription factor and an assayable product. Reporter genes encoding assayable products are readily available in the art. The assayable product may be a convenient assayable enzyme, such as chloramphenicol acetyltransferase, β-galactosidase, green fluorescence protein, or luciferase.

The transcription regulatory region or a promoter may be early or late virus promoters or constitutive promoters used in a cell. Such transcription regulatory regions are known and readily available in the art. They include but are not limited to late promoters, e.g., polyhedrin promoter and p10 promoter, early to late promoters, e.g., ETL promoter, early promoters, e.g.,immediate early gene 1 (IE1), ecdysteroid glucosyl transferase (egt) promoter, and p35 promoter, and constitutive promoters, e.g., actin promoter. The promoter may be linked with one or more copies of DNA encoding the transcription factors. Several copies of transcription factors linked with different promoters may be used. Alternatively different transcription factors linked with multiple promoters may also be used. These promoter and transcription factor combinations may be used to increase the expression of the transcription factor and the control of the modified viruses.

In a preferred embodiment, the foreign DNA is integrated into a virus genome site or a gene which is not associated with the host specificity of the virus and the function of which is dispensable to the virus. There are a number of such genes, e.g., ecdysteroid UDP-glucosyl transferase gene (egt), p10 gene, p48 gene, and polyhedrin gene, which are isolated and can be used as an integration site for foreign DNAs.

Any expression level of the transcription factor which is sufficient to cause premature and incomplete molting or abnormal insect development is contemplated in the present invention. The insect transcription factor should be expressed at a detectable level when the transgenic insect virus infects an insect. Preferably the transcription factor is expressed or overexpressed at a level higher than the physiologically needed amount in the infected insect. More preferably the transcription factor is expressed substantially in all of the insect tissues into which the transgenic viruses are introduced.

Normally, a recombinant transfer vector is constructed for making a transgenic virus. For example, a DNA fragment encoding an insect transcription factor may be covalently linked to either a viral promoter or a constitutive cell promoter, e.g., p10 promoter, via methods known in the art, e.g., restriction digestion, polymerase chain reaction (PCR), and ligation. Subsequently, the DNA fragment including the promoter and the transcription factor may be inserted into a viral gene locus, e.g., egt gene which is carried by a readily available vector, e.g., pUC18. The recombinant transfer vector may be co-transfected with an insect virus into a cell line via methods used in the art, e.g., the lipofectin method. Recombinant insect viruses containing the promoter and the transcription factor carried by the recombinant transfer vector may be determined via detecting the assayable product, the insect transcription factor, the marker gene or the promoter. The detection may be by Southern blot, Northern blot, PCR, Western blot, enzyme assay, restriction digestion, or any other method available in the art. The construction and testing of the transgenic insect virus requires no more than ordinary skill in the art.

The transgenic or recombinant viruses provided by the present invention are useful as biopesticides. The host range of the transgenic virus is determined by the natural host range of the unmodified, wild type virus. The transgenic viruses are more virulent than the wild type virus, at least 5 fold and usually 10 fold more virulent. The virulence of an insect virus can be readily determined by methods known in the art. A transgenic virus works at its maximum effect in a host insect if the transcription factor inserted into the virus is isolated from the same host insect or is the same as naturally occurs in the same host insect. Transcription factors from an insect in the same order as the host insect, or from an insect employing a similar transcription factor, may be used. The usefulness of a transcription factor may readily be determined by one skilled in the art.

Transgenic insect viruses of the present invention can be replicated and expressed inside a host insect once the virus infects the host insect. Infecting an insect with the transgenic insect viruses of the present invention can be achieved via conventional methods, including ingestion, inhalation, and direct contact of the insect or insect larvae with the transgenic insect viruses. In a preferred embodiment, the transgenic insect viruses are administered by the oral route using occlusion bodies carrying the transgenic insect viruses. In general, the amount of occlusion bodies fed to insect larvae or insect corresponds to about 0.2 to about $0.001LD_{50}$ of that species of the unmodified insect virus and insect host. The $LD_{50}$ varies with each species of insect virus and the age of the larvae, and is readily determinable by one skilled in the art.

Typically, the amount of occlusion bodies used is related to the amount of insects present in the area to be treated. Generally it will vary from about $10^3$ to about $10^{12}$ occlusion bodies per acre. Preferably, the amount is from about $10^6$ to about $10^9$ and most preferably from about $10^3$ to about $10^6$ occlusion bodies per acre. In cases in which occlusion body formation does not occur (such as when the polyhedrin gene has been used as the site for foreign gene insertion), co-infection of the insect with the budded virus forms of both transgenic and wild-type viruses provides occlusion bodies containing both recombinant and wild-type viruses and allows infection of insect larvae by the oral route.

The insecticidal composition of the invention comprises an environmentally suitable carrier and the transgenic insect viruses. The composition should be suitable for agricultural use, forest use, or any other specific use contemplated. Generally, components of the composition must be non-toxic and not detrimental to the integrity of the occluded virus. Foliar applications should not damage or injure plant leaves. In addition to appropriate solid or, more preferably, liquid carriers, the composition may include dispersants, spreader-stickers, UV protectors, insect attractants, viral enhancers, sticking and adhesive agents, emulsifiers, wetting agents, and agents which stimulate insect feeding, but not components which give non-desirable effects, e.g., deter insect feeding. Suitable carriers for insecticidal compositions are known and readily available in the art, e.g., diluents such as water, clay, and the like.

The following examples are provided for exemplification purposes only and are not intended to limit the scope of the invention.

EXAMPLE 1

Construction of Transfer Vector

As shown in FIG. 1, a CfMNPV transfer vector was created by first cloning a 6 kb fragment of CfMNPV containing egt gene into pUC18. A cassette containing AcMNPV polyhedrin and p10 promoter regions and the β-galactosidase open reading frame under a p10 promoter were then inserted in the middle of the egt gene. CHR3 cDNA was amplified using the polymerase chain reaction (PCR), with synthetic primers based on the nucleotide sequence at the N-terminal and C-terminal ends of CHR3. The restriction enzyme BagIII sites were also included in the primer sequence. The PCR product was checked on gel and found to be of the expected size. Then the PCR product was purified by passing it through a Sephadex column to remove the primers, nucleotides and other components of the PCR mix. The DNA was then digested with BagIII and repurified on a Sephadex column to eliminate the digested BagIII linkers. The digested and purified DNA was ligated to the BamHI digested CfMNPV transfer vector using T4 DNA ligase for 16 hr at 16° C. The ligated DNA was digested with BamHI to eliminate the self-ligated vector. The ligated DNA was then transformed into XLI blue cells, and the recombinant clones were screened using $^{32}$P labeled CHR3 probe (Feinberg and Vogelstein, 1984, Anal. Biochem. 137, 266–267). The DNA was isolated from positive clones and digested with BamHI. The DNA from the recombinant clones that were not linearized with BamHI and the two CHR3 primers were used in a PCR procedure to verify the size of the insert. The insert in the recombinants was of the expected size. Then the DNA from the recombinants was sequenced using dideoxy termination method. The nucleotide sequence was identical to that of CHR3 on both the 5' and 3' ends. One clone in each orientation was selected for transfer into CfMNPV.

EXAMPLE 2

Production of Recombinant Viruses

Figure 2B:
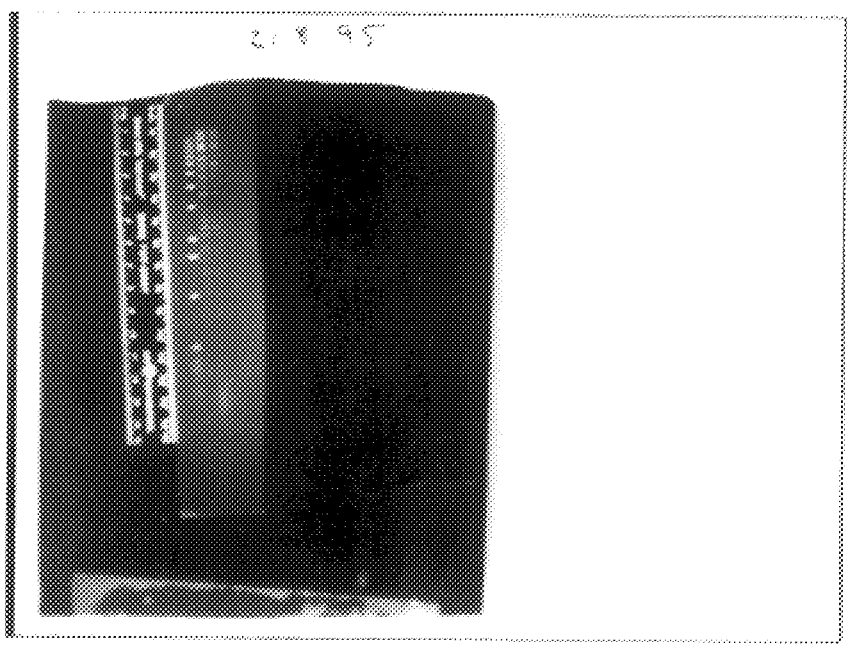

The CfMNPV DNA and the recombinant transfer vector DNA (CHR3 in sense and antisense orientations) were co-transfected into CF-124T cells using the lipofectin method. The medium was collected one week after transfection and used as an inoculum for plaque purifying recombinant viruses. For plaque purification, various dilutions of the recombinant budded viruses (BV) were plated on CF-203 cells. A week after infection the plates were stained with X-gal. The areas of blue color observed at the lowest dilution were picked and replaqued. This procedure was repeated 4 times. Two viruses, expressing the CHR3 in the sense and antisense orientations, were obtained. The plaque purified viruses were then amplified in CF-203 cells. The DNA was isolated from the BV, digested with HindIII, and separated on an agarose gel. The DNA from the gel was transferred to Hybond-N membrane and probed with $^{32}$P-labeled CHR3 probe. As shown in FIG. 2, one band that hybridized to CHR3 probe was observed in the digests of the recombinant viral DNA but not in the wild-type CfMNPV DNA. Comparison of the HindIII digestion pattern of the recombinants with that of the wild-type CfMNPV DNA showed that the CHR3 DNA was inserted at the expected region of CfMNPV. The DNA isolated from the recombinant viruses and the CHR3 primers were used in a PCR procedure to verify the size of the CHR3 insert in the recombinant viruses. Both viruses were found to contain an insert of the expected size. The PCR amplified DNA was then sequenced, the nucleotide sequence was identical to that of CHR3.

EXAMPLE 3

Time Course of CHR3 Expression

Figure 3:
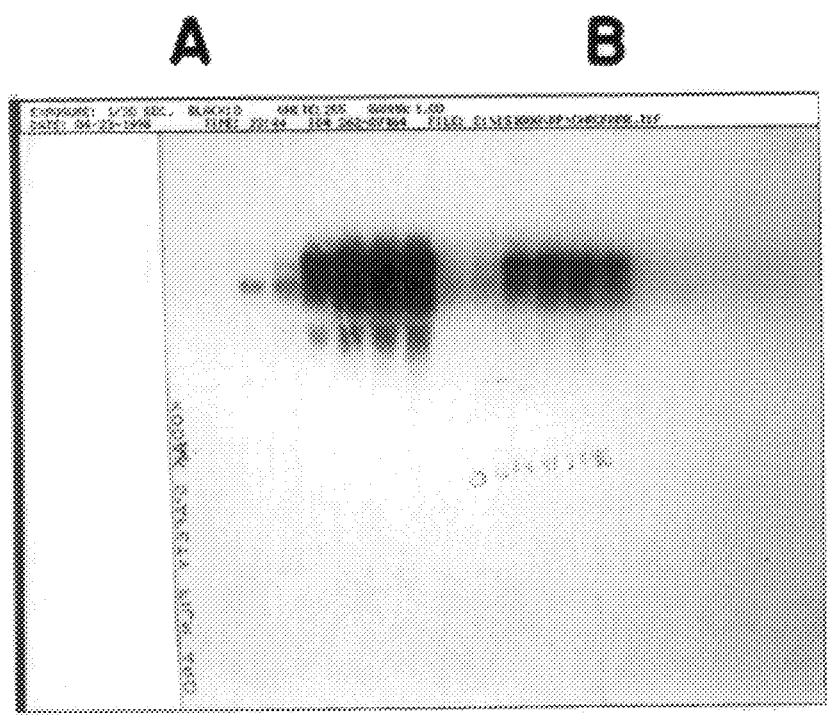
FIG. 3 shows the time course of CHR3 expression in cells infected with recombinant viruses.

To study the time course of CHR3 expression in CF-203 cells infected with recombinant viruses, CF-203 cells were inoculated with the recombinant virus expressing CHR3 in the sense or antisense orientation. The cells were collected at 0, 6, 12, 24, 48, 72, and 96 hr after inoculation. Total RNA was isolated and analyzed by Northern hybridization, using CHR3 cDNA as a probe. As shown in FIG. 3, CHR3 mRNA started accumulating in cells at 24 hr after inoculation with either of the two recombinant viruses. The mRNA levels remained high until 96 hr after inoculation.

EXAMPLE 4

Evaluation of Recombinant Viruses for Insecticidal Activity

In the first trial, 1×10$^5$ occlusion bodies (OB) isolated from CF-203 cells inoculated with recombinant virus expressing CHR3 either in the sense or antisense orientations were fed to 5th larval instar *Choristoneura fumiferana*. Two to three days after the larvae were fed the recombinant virus expressing CHR3 in the sense orientation, 8 out of the 10 larvae showed head capsule slippage (HCS) and remained in a moribund state, and the other two died as 5th instar larvae. The larvae that showed head capsule slippage had an untanned head capsule, stopped feeding, remained moribund, and eventually died. In some cases the hind gut protruded out through the anal end. These symptoms are similar to the symptoms shown by larvae intoxicated with nonsteroidal ecdysone agonists such as tebufenozide. None of the larvae that fed on the recombinant virus expressing CHR3 in the antisense orientation showed these symptoms. The virus obtained from the insects that showed symptoms of partial molting was isolated and used in the second and third bioassays as shown in Tables 1 and 2. The larvae that fed on the recombinant virus at a dose as low as 1000 OB inhibited the typical symptoms of incomplete molt.

TABLE 1

| Dosage (OB's/insect) | # insects treated | # dead no HCS | # dead HCS L5 | # dead HCS L6 | # Healthy | % Dead |
|---|---|---|---|---|---|---|
| 1000 | 3 | 0 | 0 | 3 | 0 | 100 |
| 5000 | 5 | 0 | 5 | 0 | 0 | 100 |
| 10000 | 5 | 0 | 4 | 1 | 0 | 100 |
| 20000 | 5 | 0 | 5 | 0 | 0 | 100 |
| 50000 | 4 | 1 | 3 | 0 | 0 | 100 |
| 100000 | 2 | 0 | 2 | 0 | 0 | 100 |

TABLE 2

| Dosage (OB's/insect) | # Insects treated | # Dead | # Healthy | % Mortality |
|---|---|---|---|---|
| 0 | 19 | 1 | 18 | 5.3 |
| 1000 | 20 | 16 | 4 | 80.0 |
| 5000 | 18 | 18 | 0 | 100.0 |
| 10000 | 16 | 14 | 2 | 87.5 |
| 20000 | 13 | 13 | 0 | 100 |
| 50000 | 18 | 18 | 0 | 100 |
| 100000 | 8 | 8 | 0 | 100 |

EXAMPLE 5

Production of *Autographa californica* nucleopolyhedrovirus (AcMNPV) expressing Manduca hormone receptor 3 (MHR3).

Figure 4:
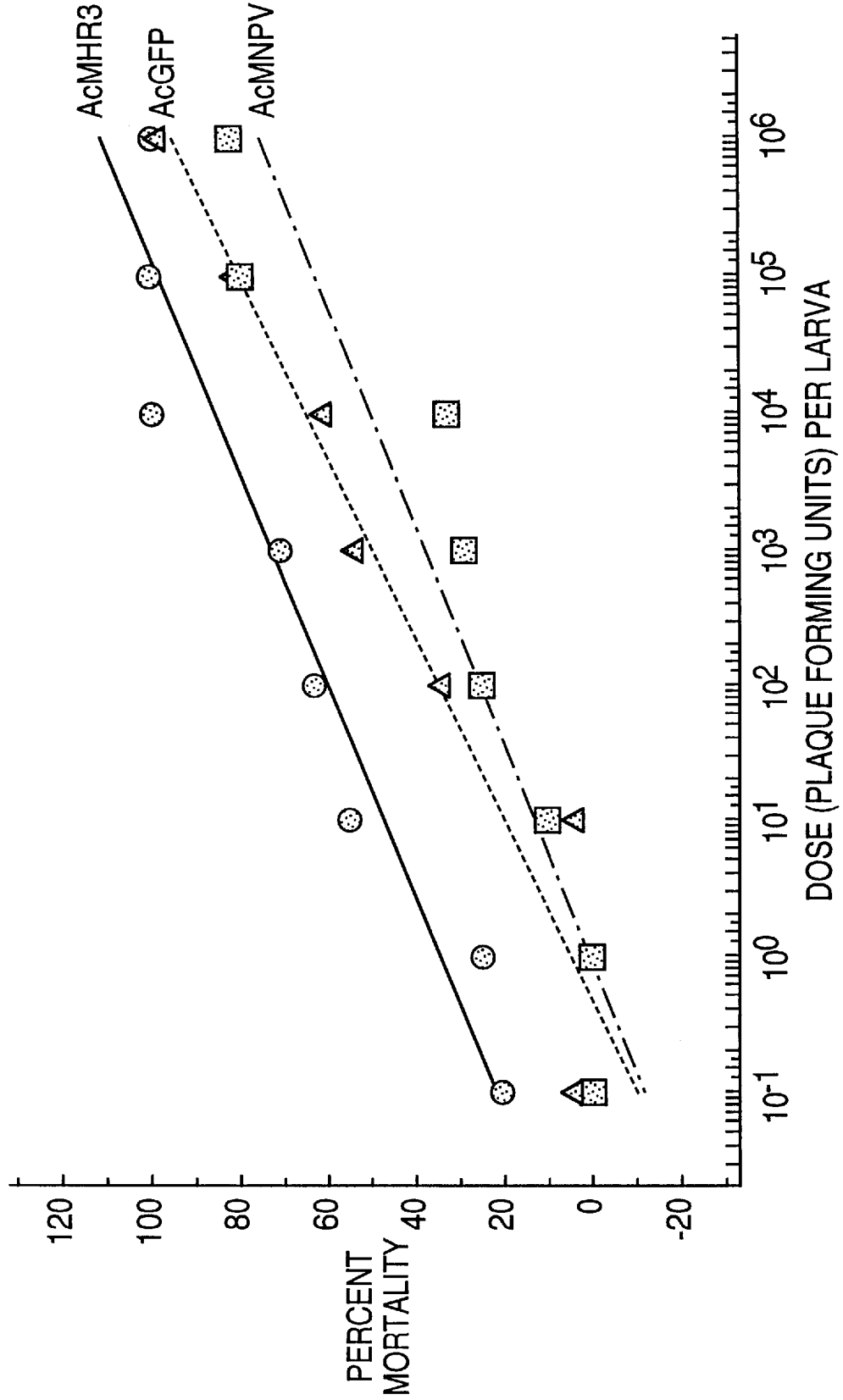
FIG. 4 shows the effect of AcMHR3 in bioassays. AcMNPV (●) denotes the unmodified virus, AcGFP (▲) denotes a AcMNPV recombinant expressing green fluorescence protein, and AcMHR3 (■) denotes a AcMNPV recombinant expressing the transcription factor MHR3.

We have constructed a recombinant AcMNPV expressing MHR3. MHR3 cDNA (Palli et al., 1992 Dev. Biol.) was isolated via restriction enzyme digestion, i.e., EcoRI and XhoI digestion, and cloned into EcoRI and XhoI sites of AcMNPV transfer vector pFASTBACI (Life Technologies INC.). The AcMNPV recombinant expressing MHR3 was then identified following the procedures supplied by the manufacturer (Life Technologies INC). The presence of MHR3 DNA in the AcMHR3 recombinant was verified by Southern blot hybridization using MHR3 cDNA as a probe. The titre of the virus was determined by plaque assay procedure. The insect cell line, *Spodoptera frugiperda* 9 cells (ATCC CRL-1711) cultured in SF-900 medium, were inoculated with AcMHR3 recombinant multiplicity of infection (MOI) of one. The cells were harvested at 12, 24, 48, 72, and 96 hr post inoculation. RNAs were isolated from one set of cell samples, resolved on a 1.0% agarose formaldehyde gel, transferred to Hybond-N membrane, and probed with MHR3 cDNA under Northern hybridization conditions. Proteins were isolated from another set of cell samples and analyzed on Western blots using MHR3 antibodies. MHR3 RNA was detected in AcMHR3 inoculated SF-9 cells beginning at 12 hr pi and MHR3 protein was detected beginning at 24 hr pi. The recombinant AcMHR3 was then evaluated by a bioassay procedure on *Trichoplusia ni larvae*. Unmodified AcMNPV and AcMNPV recombinants expressing green fluorescence protein (GFP), constructed similarly to AcMHR3, were used to compare with AcMHR3 in the bioassay. Penultimate instar *T. ni larvae* were injected with 1 µl of solution containing certain amount of virus (plaque forming units). After injection, the larvae were transferred to diet cups and observed daily until they died or pupated. As shown in FIG. 4, the AcMHR3 killed the insects and worked 1000× better than AcMNPV. AcGFP worked only 15× better than AcMNPV.

The principles, preferred embodiments, and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A transgenic insect virus selected from the group consisting of entomopoxvirus A, entomopoxvirus B, and baculovirus, containing foreign DNA which encodes a developmental, hormone regulated, insect transcription factor and which is operably linked to a transcription regulatory region.

2. The transgenic insect virus of claim 1 wherein the insect transcription factor is associated with insect molting and metamorphosis.

3. The transgenic insect virus of claim 1 wherein the foreign DNA encodes a fusion protein comprising a developmental, hormone regulated, insect transcription factor and an assayable product.

4. The transgenic insect virus of claim 1 wherein the insect transcription factor is selected from the group consisting of Drosophila BR-C, E74, E75, Ultraspiracle, E78, Sevenup, Kni/Knrl/egon, FTZ-F1, DHR38, E93, Relish-antibacterial transcription factor, Col-head patterning transcription factor, Escargot and snail transcription factors, Dorsal transcription factors, DSX-M and DSX-F transcription factors, Dif, Eyeless transcription factors, Gap gene kni transcription factors, Kappa B like immune genes activating transcription factor, transcription factors encoded by Zygotic genes that regulate embryonic development of the anterior and posterior termini, DHR78, DHR96, Manduca MHR3-ecdysone inducible transcription factor, Choristoneura hormone receptor 2 (CHR2), Choristoneura hormone receptor 3 (CHR3), *Choristoneura fumiferana* ecdysone receptor (CfEcR), *Choristoneura fumiferana* ultraspiracle protein (CfuSP), Spodoptera Viral gp64 activating transcription factor, Egr-1 master switch gene, and Bombyx Mori Silk protein transcription factor.

5. The transgenic insect virus of claim 2 wherein the insect transcription factor is selected from the group consisting of Choristoneura hormone receptor 2 (CHR2), Choristoneura hormone receptor 3 (CHR3), *Choristoneura fumiferana* ecdysone receptor (CfEcR), *Choristoneura fumiferana* ultraspiracle protein (CfUSP), Manduca hormone receptor 3 (MHR3), and Drosophila hormone receptor 38 (DHR38).

6. The transgenic virus of claim 1 wherein the developmental hormone is selected from the group consisting of ecdysone and juvenile hormone.

7. The transgenic insect virus of claim 1 wherein the transcription regulatory region is selected from the group consisting of p10 promoter, polyhedrin promoter, ETL promoter, IE1 promoter, egt promoter, p35 promoter, and actin promoter.

8. The transgenic insect virus of claim 1 wherein the foreign DNA resides within a viral gene selected from the group consisting of polyhedrin gene, p10 gene, p48 gene, and ecdysteroid glucosyl transferase gene.

9. The transgenic insect virus of claim 1 wherein the insect transcription factor is expressed in an insect infected with the transgenic insect virus of claim 1.

10. An insecticidal composition comprising the transgenic insect virus of claim 1 and an environmentally suitable carrier.

11. A method of treating an insect pest comprising administering the insecticidal composition of claim 10 to an area containing the insect pest.

12. The method of claim 11 wherein the transgenic virus contains foreign DNA encoding the developmental, hormone regulated, insect transcription factor which naturally occurs in said insect.

13. A method of causing abnormal development of an insect comprising infecting as insect with the insect transgenic virus of claim 1.

14. The method of claim 13 wherein the transgenic virus contains foreign DNA encoding the developmental, hormone regulated, insect transcription factor which naturally occurs in said insect.

* * * * *